United States Patent
Schwartz et al.

(10) Patent No.: US 10,952,987 B2
(45) Date of Patent: Mar. 23, 2021

(54) COMBINATION OF ADRENALIN WITH AN ANTIDEPRESSANT FOR USE IN THE TREATMENT OF SHOCKS

(71) Applicant: BIOPROJET, Paris (FR)

(72) Inventors: Jean-Charles Schwartz, Paris (FR); Xavier Ligneau, Saint Grégoire (FR); Laurent François Gérard Landais, Ercé-Près-Liffré (FR); David Perrin, Gévezé (FR); Jeanne-Marie Lecomte, Paris (FR)

(73) Assignee: BIOPROJET, Paris (FR)

( * ) Notice: Subject to any disclaimer, the term of this patent is extended or adjusted under 35 U.S.C. 154(b) by 0 days.

(21) Appl. No.: 16/223,750

(22) Filed: Dec. 18, 2018

(65) Prior Publication Data

US 2019/0117614 A1    Apr. 25, 2019

Related U.S. Application Data

(62) Division of application No. 14/433,549, filed as application No. PCT/EP2013/070598 on Oct. 2, 2013, now abandoned.

(30) Foreign Application Priority Data

Oct. 3, 2012   (EP) .................................. 12306207

(51) Int. Cl.
| A61K 31/335 | (2006.01) |
| A61K 45/06  | (2006.01) |
| A61K 31/137 | (2006.01) |
| A61K 9/00   | (2006.01) |

(52) U.S. Cl.
CPC .......... *A61K 31/335* (2013.01); *A61K 9/0019* (2013.01); *A61K 31/137* (2013.01); *A61K 45/06* (2013.01)

(58) Field of Classification Search
CPC .................................................. A61K 31/335
USPC .......................................................... 514/450
See application file for complete search history.

(56) References Cited

PUBLICATIONS

Weeke et. al. (Clinical Pharmacology and Therapeutics (2012) 92:72-79). (Year: 2012).*
Ababneh et. al. (Birth Defect Research (2012) 95:184-193). (Year: 2012).*
Citak et. al. (Pediatrics International (2006) 48:582-585). (Year: 2006).*
Frank et. al. (The International Journal of Artificial Organs (2000) 23:618-623.) (Year: 2000).*
Elonen et. al. (Medical Biology (1975) 53:238-244). (Year: 1975).*
Elonen et. al. (European Journal of Pharmacology (1974) 28:178-188). (Year: 1974).*

* cited by examiner

*Primary Examiner* — Marcos L Sznaidman
(74) *Attorney, Agent, or Firm* — B. Aaron Schulman, Esq.; Stites & Harbison, PLLC

(57) ABSTRACT

The present invention concerns a novel combination of adrenalin with an antidepressant and its use as a pharmaceutical composition for the treatment of shocks. A method is also provided for treating a subject in need thereof by administering the combination of adrenaline with an antidepressant. The pharmaceutical composition is to be administered by injection.

10 Claims, 1 Drawing Sheet

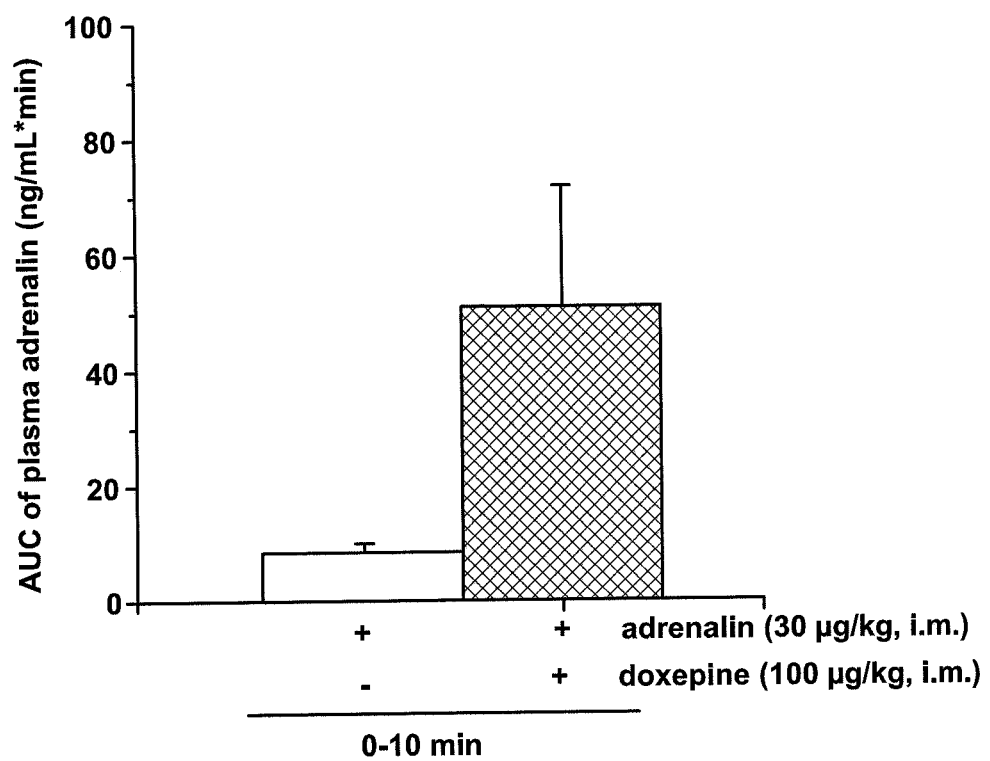

COMBINATION OF ADRENALIN WITH AN ANTIDEPRESSANT FOR USE IN THE TREATMENT OF SHOCKS

CROSS-REFERENCE TO RELATED APPLICATIONS

This application is a divisional of U.S. patent application Ser. No. 14/433,549, having a filing date of Apr. 3, 2015, which is a 371 application of International Application PCT/EP2013/070598, filed Oct. 2, 2013, and which claims the benefit of European Application Ser. No. 12306207.7, filed Oct. 3, 2012, all of said applications incorporated herein by reference.

Circulatory shocks, commonly known as "shocks", are life-threatening medical emergencies wherein the organs and tissues of the body are not receiving an adequate flow of blood and thus an adequate level of oxygen. There are three major types of shocks: cardiogenic, hypovolemic, and distributive shocks. Among distributive shocks, the anaphylactic shock and septic shock can be cited.

Among the symptoms of shocks, it can be cited tachycardia, hypotension and signs of poor end-organ perfusion such as low urine output, confusion or weakness.

In one embodiment, the present invention concerns a novel combination of adrenalin with an antidepressant for use in the treatment of shocks, for which the emergency treatment comprises the administration of adrenalin.

Among these shocks, the anaphylactic shock can be cited. Anaphylaxis is a severe allergic reaction of rapid onset affecting many body systems and may cause death. It is due to the release of inflammatory mediators and cytokines from mast cells and basophils, typically due to an immunologic reaction but also, sometimes, non-immunologic mechanisms.

In the immunologic mechanism, immunoglobulin E (IgE) binds to an antigen. Antigen-bound IgE then activates FcεR1 receptors (Fc epsilon RI receptors) on mast cells and basophils. This leads to release of inflammatory mediators such as histamine. These mediators subsequently increase the contraction of bronchial smooth muscles, trigger vasodilation, increase the leakage of fluid from blood vessels, and cause heart muscle depression.

Non-immunologic mechanisms involve substances that directly cause the degranulation of mast cells and basophils. These include agents such as contrast media, penicillins, opioids, temperature (hot or cold), and vibration.

The prevalence of severe anaphylaxis is high and dramatically increasing each year. For instance, in France, a recent publication (Monneret-Vautrin, Rev. Fr. Allerg. Immunol. Clin. 2008, 48, 171) quotes a prevalence of 1/10,000 inhabitants and a mortality of 1 per million inhabitants, thereby illustrating the seriousness of the problem.

The balance of evidence from human observations and animal studies suggests that the main pathophysiologic features of anaphylactic shock are a profound reduction in venous tone and fluid extravasation causing reduced venous return (mixed hypovolemic-distributive shock) and depressed myocardial function.

In the occurrence of shocks and more particularly of anaphylactic reactions, an injection of adrenalin (also called epinephrine or adrenaline) within minutes of the onset of symptoms can be lifesaving (Kemp S F et al. *Allergy*, 2008, 63, 1061-1070). Administration of adrenalin will increase vascular tone, myocardial contractility, and cardiac output in most cases. Adrenalin is a well-known emergency treatment of circulatory shocks such as anaphylactic shock, cardiac arrest, and cardiovascular distress associated with anaphylactic shock, hemorragic shock, traumatic shock, infectious shock and secondary shock due to cardiac surgery.

Nevertheless, this treatment is not always successful. Therefore, there is a need to provide a new and improved treatment of shocks and more particularly of the anaphylactic shock.

The inventors have found that among other reasons, the treatment by adrenalin may fail due to the delay required for the injected adrenalin dose to reach the general circulation from the injected site. In agreement plasma levels of adrenalin increase slightly a few minutes after such injection but the bulk of the increase occurs after a delay of about 20 minutes in animals as well as in humans (Simons et al. J Allergy Clin Immunol. 2001; 108:871-3.). Such a delay for the second peak seems attributable to the local vasoconstriction elicited by adrenalin at the injection site.

Therefore, the inventors have hypothesized that the diffusion of adrenalin in general circulation could be improved by the inhibition of the alpha-1 adrenergic receptor and/or by the inhibition of adrenalin capture by the noradrenalin/monoamine transporters.

Moreover, in the particular case of anaphylactic shock and among the other mechanisms involved in this type of shock, the release of histamine plays an important role, as histamine triggers particularly the inflammatory response. There are four types of histaminergic receptors H1, H2, H3 and H4. H1 histaminergic receptors (H1-receptors or H1R) are found on smooth muscle and endothelium, and are particularly responsible for bronchial smooth muscle contraction, plasma extravasation and vasodilatation during anaphylactic shock. Therefore, acting on H1-receptors may be of interest in the treatment of the anaphylactic shock. A treatment of anaphylactic shock which presents an action on several or all mechanisms involved in the anaphylactic shock may thus be of great interest.

Drugs interactions between catecholamines such as adrenalin or noradrenalin and antidepressants are well-known. The antidepressants are known to potentiate the pressor effects of adrenalin (see Boakes A. J et al. 1973, *British Medical Journal*, 1, 311-315 and Svedmyr, N. 1968, *Life Sciences* vol. 7, pp. 77-84).

However, in these drug interactions studies, adrenalin and antidepressants are administrated separately, to recreate the usual conditions of medication (long-term treatment for the antidepressant): the antidepressant is administered several times a day for several days before the administration of adrenalin by intravenous route.

Other studies dealt with drugs interactions between noradrenalin and antidepressants, administered simultaneously by intravenous route (see Elonen E. and Mattila M. J., 1975, *Medical Biology* 53, 238-244, and Elonen E. et al., 1974, *European Journal of Pharmacology*, 28, 178-188).

The conditions of administration described in the above-mentioned studies are however not suitable for treating shock as this condition requires a quick administration of the drug and the intravenous route is not suitable for such an urgency situation. In shocks, the injection should be done as quickly as possible, most often by the person herself or untrained staff. Hence the above experimental studies do not describe the administration of adrenalin together with an antidepressant by the patient himself during the course of a shock. Further, any effect on the speed of blood bioavailability of subcutaneous or intramuscular adrenalin provided by co-administering the antidepressant cannot obviously be predicted from studies in which adrenalin is administered simultaneously with the antidepressant by intravenous route, i.e. directly into blood.

It is an object of the present invention to provide a new and improved treatment for shocks, particularly an improved treatment in which the rate of diffusion of adrenalin from its site of injection to the general circulation is improved.

It is an object of the present invention to provide a new and improved treatment for the anaphylactic shock, particularly an improved treatment in which the rate of diffusion of adrenalin from its site of injection to the general circulation is improved.

It is an object of the present invention to provide a new treatment for shocks in which the bioavailability of adrenalin is improved.

It is an object of the present invention to provide a new treatment for the anaphylactic shock in which the bioavailability of adrenalin is improved.

It is another object of the present invention to provide a treatment of the anaphylactic shock that acts on several mechanisms involved in anaphylactic shock.

It is another object of the invention to provide a treatment of anaphylactic shock which acts on H1 histaminergic receptors.

It is another object of the present invention to provide a pharmaceutical composition suitable for intramuscular and/or subcutaneaous injection useful in the treatment of shocks.

It is another object of the present invention to provide a pharmaceutical composition suitable for intramuscular and/or subcutaneaous injection useful in the treatment of anaphylactic shock.

It is another object of the present invention to provide an auto-injection device useful in the treatment of shocks.

It is another object of the present invention to provide an auto-injection device useful in the treatment of anaphylactic shock.

Surprisingly, the present inventors discovered that the combination of adrenalin with an antidepressant improves the diffusion of adrenalin into the general circulation, leading to a rapid and sustained plasma level. Also, the combination of adrenalin with an antidepressant accelerates the diffusion of adrenalin into general circulation, and/or blocks the main deleterious actions of released histamine.

The combination of adrenalin and an antidepressant according to the invention is preferably administered by intramuscular or subcutaneous injection.

The combination of adrenalin with an antidepressant preferably administered together via intramuscular or subcutaneous route potentiates the action of adrenalin, thus involving a synergy between the two active ingredients. Such effects are of great interest as they can be life-saving.

Therefore, one of the advantages of the invention is that the administration of adrenalin with the antidepressant is easy to perform. Another advantage of the combination according to the invention is the local effect of the antidepressant that prevents the local vasoconstriction at the adrenalin site of injection, leading to an improved bioavailability of adrenalin.

The invention therefore allows the combination of a ready-to-use treatment of shocks with an improved bioavailability in the first ten minutes following the intramuscular or subcutaneous injection of the combination adrenalin-antidepressant.

The combination according to the invention is thus of great interest in shocks for which the treatment comprises the quick administration of adrenalin as it improves the bioavailability of adrenaline, and can thus be life-saving.

The present invention thus relates to an aqueous solution comprising adrenalin and an antidepressant.

Adrenalin (or epinephrine) is both a hormone and a neurotransmitter. It belongs to the group of catecholamines. Adrenalin as used herein refers to the formula:

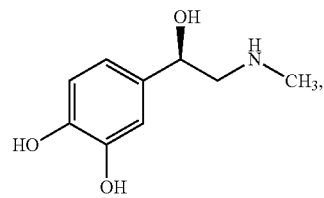 [SMILES: CNC[C@H](O)c1ccc(O)c(O)c1]

as well as its pharmaceutically acceptable salts.

The term <<antidepressant>> refers to an active principle which is used for the prevention and/or treatment of depression. Depression is a mood disorder characterized by an all-encompassing low mood accompanied by low self-esteem, and by loss of interest or pleasure in normally enjoyable activities.

In one embodiment, the antidepressant is an inhibitor of noradrenalin/monoamine transporters as well as an antagonist of the alpha-1 adrenergic receptors and an antagonist of the H1 receptors.

By "antagonist of the H1 receptor" is meant a compound generally having a Ki inferior to 35 nM for the H1-receptors. By "antagonist of the alpha-1 adrenergetic receptor" is meant a compound having a Ki inferior to 200 nM for the alpha-1 adrenergetic receptors. By "inhibitor of the noradrenalin/monoamine transporter" is meant a compound having a Ki inferior to 100 nM for the noradrenalin/monoamine transporters.

By "Ki" is meant the dissociation constant obtained by inhibiting the binding of a ligand or the inhibition constant obtained by inhibiting noradrenalin/adrenalin uptake.

The Antidepressant can be Chosen Among the Following Classes:
Serotonin-norepinephrine reuptake inhibitors (SNRIs),
Serotonin antagonist and reuptake inhibitors (SARIs),
Norepinephrine reuptake inhibitors (NRIs),
Norepinephrine-dopamine reuptake inhibitors (NDRIs),
Norepinephrine-dopamine releasing agents (NDRAs),
Tricyclic antidepressants (TCAs), and
Tetracyclic antidepressants (TeCAs).

In one embodiment, the antidepressant is chosen among the tricyclic antidepressants (TCAs) or one of their pharmaceutically acceptable salts.

TCAs Include in Particular:
amitriptyline, amoxapine, amitriptylinoxide, butriptyline, clomipramine, demexiptiline, desipramine, dibenzepin, dimetacrine, dosulepin/dothiepin, doxepin, imipramine, imipraminoxide, lofepramine, maprotiline, mianserin, melitracen, metapramine, nitroxazepine, nortriptyline, noxiptiline, pipofezine, propizepine, protriptyline, quinupramine, amineptine (norepinephrine-dopamine reuptake inhibitor), and trimipramine.

In one embodiment, TCAs include:
amitriptyline, amoxapine, amitriptylinoxide, butriptyline, clomipramine, demexiptiline, dibenzepin, dimetacrine, dosulepin/dothiepin, doxepin, imipraminoxide, lofepramine, maprotiline, mianserin, melitracen, metapramine, nitroxazepine, nortriptyline, noxiptiline, pipofezine, propizepine, protriptyline, quinupramine, amineptine (norepinephrine-dopamine reuptake inhibitor), and trimipramine.

In another embodiment, the antidepressant is chosen among the group consisting of:

amitryptyline, amoxapine, clomipramine, doxepin, imipramine, maprotiline, mianserin nortriptyline, protriptyline and trimipramine. More preferably the antidepressant is chosen among the group consisting of doxepin, trimipramine, amitriptyline and mianserin. More preferably, the antidepressant is chosen among doxepin or one of its pharmaceutically acceptable salts, preferably doxepin chlorhydrate, imipramine or one of its pharmaceutically acceptable salts, preferably imipramine chlorhydrate or amitryptiline or one of its pharmaceutically acceptable salts, preferably amitryptiline chlorhydrate.

In a preferred embodiment, the antidepressant is doxepin or doxepin chlorhydrate.

The term "pharmaceutically acceptable salts" refers to salts which retain the biological effectiveness and properties of the active ingredient and which are not biologically or otherwise undesirable. Pharmaceutically acceptable acid addition salts may be prepared from inorganic and organic acids, while pharmaceutically acceptable base addition salts can be prepared from inorganic and organic bases. For a review of pharmaceutically acceptable salts see Berge, et al. ((1977) J. Pharm. Sd, vol. 66, 1). For example, the salts include those derived from inorganic acids such as hydrochloric, hydrobromic, sulfuric, sulfamic, phosphoric, nitric, and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, methanesulfonic, and toluenesulfonic acid and the like. The preferred pharmaceutically acceptable salts for the antidepressant are chosen among chlorhydrate, mesilate, maleate and fumarate. The preferred pharmaceutically acceptable salts for adrenalin are chlorhydrate and tartrate.

The present invention also encompasses hydrates or hydrated salts or polymorphic crystalline structures, racemates, diastereomers or enantiomers of the active ingredients.

In one embodiment, the solution of the invention further comprises one or more pharmaceutically acceptable excipient(s) such as preservative agents, buffers, substance to make the solution isotonic with blood such as sodium chloride, solvents, stabilizers, or antimicrobial preservatives. It can be cited: sodium, hydrochloric acid or water for injection. The excipients used are well-known to the skilled person. They should not adversely affect the stability, bioavailability, safety, or efficacy of the active ingredients, or cause toxicity or undue local irritation when the solution is to be administered by injection. In a particular embodiment, the solution of the invention further comprises at least one preservative agent. In a preferred embodiment, the preservative agents are chosen among sodium metabisulfite, sodium bisulfite, ascorbic acid and/or their mixture. Preferably, the preservative agent is sodium metabisulfite.

In a particular embodiment, the solution of the invention consists of adrenalin, an antidepressant, sodium chloride, a preservative agent and water.

In one embodiment, in the solution of the invention, adrenalin is at a concentration comprised between 0.05 mg/ml and 1.0 mg/ml. In a particular embodiment, adrenalin is at a concentration between 0.15 mg/ml and 1.0 mg/ml. In another embodiment, adrenalin is at a concentration between 0.6 mg/ml and 1.0 mg/ml in formulations suitable for adults.

In another embodiment, adrenalin is at a concentration between 0.1 mg/ml and 0.6 mg/ml in formulations suitable for children.

In another embodiment, in the solution as defined above, the antidepressant is at a concentration comprised between 0.1 mg/ml and 10 mg/ml. Preferably, the antidepressant is at a concentration comprised between 0.3 mg/ml and 3 mg/ml.

The invention also relates to a pharmaceutical composition comprising the solution as defined above. In a preferred embodiment, the invention relates to a pharmaceutical composition comprising the solution as defined above, wherein the solution is suitable for injection. An injection is an instrumental method used to introduce into the body a liquid pharmaceutical composition by parenteral administration.

By injection is preferably meant a method of administration into a subject in need thereof which can be intramuscular, subcutaneous or a transcutaneous penetration. By transcutaneous penetration is to be understood an injection by local pressure using devices without skin perforation by needle. More preferably, the pharmaceutical composition of the invention is suitable for intramuscular injection and/or subcutaneous injection. Preferably, the pharmaceutical composition as defined above is administered by intramuscular injection. In one embodiment, the injection of the above defined pharmaceutical composition is not an intravenous injection.

In one embodiment, the pharmaceutical composition of the invention is in a unit dosage form in which the injected volume is comprised between 0.1 ml and 0.5 ml. More preferably, the injected volume is of 0.3 ml.

The invention also relates to the pharmaceutical composition as defined above, for use in the treatment of shocks.

The invention also relates to the use of a solution as defined above for the preparation of a pharmaceutical composition to treat shocks.

The invention also relates to the solution as defined above for its use in the treatment of shocks.

By "shock" it is understood a circulatory shock, which may be characterized by a decrease of the organ perfusion. Circulatory shocks are acute and severe pathologies, often life-threatening, and are well-known by physicians.

The term "shock" refers to every shock as defined herein, for which the emergency treatment comprises the administration of adrenalin, more particularly for which adrenalin is administered by injection, subcutaneously or by intramuscular route.

In one particular embodiment, the shock is chosen from the group consisting of: anaphylactic shock, cardiac arrest, and cardiovascular distress associated with anaphylactic shock, hemorragic shock, traumatic shock, infectious shock and secondary shock due to cardiac surgery. In a particular embodiment, the shock is the anaphylactic shock.

In one particular embodiment, the solution and/or the pharmaceutical composition as defined above is used in the treatment of a pathology chosen from the group consisting of: anaphylactic shock, cardiac arrest, and cardiovascular distress associated with anaphylactic shock, hemorragic shock, traumatic shock, infectious shock and secondary shock due to cardiac surgery. In a particular embodiment, the pathology is the anaphylactic shock.

By "treatment", it may be understood the treatment of the causes of the shock and/or the treatment of its symptoms, more particularly the treatment of its symptoms.

In another embodiment, the use of the pharmaceutical composition as defined above, comprises administering a dose of adrenalin comprised between 0.05 mg and 0.35 mg. Preferably, the use of the pharmaceutical composition as defined above, comprises administering a dose of adrenalin comprised between 0.05 mg and 0.15 mg for children and between 0.1 mg and 0.30 mg for adults. More preferably, the use of the pharmaceutical composition as defined above comprises administering a dose of adrenalin of 0.1 mg for children and of 0.2 mg for adults.

In another embodiment, the pharmaceutical composition for use as defined above, comprises administering the antidepressant at a dose comprised between 0.1 mg and 3 mg.

The exact dosage between these limits will be defined in human trials in which the dose ratio of the two active constituents will be varied in order to obtain the optimal efficacy of adrenalin and best safety.

In another embodiment, the unit dosage form is contained in an auto-injection device. Auto-injection devices or auto-injectors are medical devices designed to deliver a single dose of a pharmaceutical composition. They are easy and ready to use and are intended for self-administration by patients, or administration by untrained personnel. The site of injection depends on the pharmaceutical composition, but it typically is administered into the thigh or the buttocks. Auto-injection devices for adrenalin are well-known by a man skilled in the art such as Anapen®, Epipen®, Twin-ject®, Intelliject® or Crossject®. They allow the administration of injectable solutions by intramuscular injection, subcutaneous injection or transcutaneous penetration.

The invention thus also relates to an auto-injection device comprising the pharmaceutical composition of the invention.

In one embodiment, the auto-injection device comprises a container prefilled with the pharmaceutical composition as defined above. Preferably, said container is a prefilled syringe.

In another embodiment, the auto-injection device comprises two containers wherein one container is prefilled with an aqueous solution of adrenalin, the other one container is prefilled with an aqueous solution of an antidepressant and wherein the pharmaceutical composition of the invention is formed by mixing the two solutions within the device. This particular embodiment allows when performing the injection, the administration of the two solutions at the same time and at the same point of injection. Said aqueous solutions may be the commercially available solutions for injection comprising adrenalin on one hand and the antidepressant on the other hand and/or may exhibit similar concentrations, dosage unit forms, excipients as the solution of the invention disclosed above.

In a particular embodiment, the auto-injection device as defined above comprises at least one prefilled container which is (are) suitable for injection of a volume of the pharmaceutical composition as defined above comprised between 0.1 ml and 0.5 ml. Preferably, the injected volume of the pharmaceutical composition of the invention is of 0.3 ml.

In one embodiment, an aqueous solution of adrenalin and another aqueous solution of antidepressant may also be separate, provided they are administered at the same time, and at the same point of injection. By "same point of injection" is understood the area of action of the antidepressant which is the area where the antidepressant blocks totally or partially the local vasoconstriction induced by injected adrenalin, therefore accelerating the systemic bioavailability and potentiating the activity of adrenalin. By "same time" is meant the time of action of the antidepressant which is the time it takes for the antidepressant to block totally or partially the local vasoconstriction induced by injected adrenalin, therefore accelerating the systemic bioavailability and potentiating the activity of adrenalin.

The present invention also encompasses the combination of these separate aqueous solutions for use for the treatment of shocks for simultaneous administration.

In one embodiment, the combination of these separate aqueous solutions is used for the treatment of anaphylactic shock for simultaneous administration.

Thus, the invention also relates to an auto-injection device comprising two containers wherein the pharmaceutical composition of the invention is prepared from an aqueous solution of adrenalin and an aqueous solution of an antidepressant, one container being prefilled with the aqueous solution of adrenalin, the other one container being prefilled with the aqueous solution of the antidepressant. The containers are preferably prefilled syringes.

The invention also relates to a method of treatment of shocks comprising the administration of a pharmaceutical composition as defined above in a patient in need thereof.

In one embodiment, the invention also relates to a method of treatment of the anaphylactic shock comprising the administration of a pharmaceutical composition as defined above in a patient in need thereof.

The increased efficacy of such novel association of adrenalin with an antidepressant was evidenced in several animal models described in the following examples. The following examples are presented as particular embodiments of the invention and cannot be considered as a limitation to the present invention.

DESCRIPTION OF THE FIGURES

FIG. 1 shows the bioavailability of adrenalin when the combination according to the invention is injected in rabbits compared with adrenalin injected alone during the 10 minutes following the injection.

EXAMPLES

Example 1: Synergy of the Combination of Adrenalin with an Antidepressant in Rabbits Protocol:

In anesthetized rabbits an intramuscular injection into the thigh of 30 µg/kg of adrenalin alone in 0.3 ml of aqueous solution was performed. The same protocol was used with the same dose of adrenalin associated with 0.1 mg/kg of doxepin. Plasma levels of adrenalin and mean blood pressure were noted down.

Results:
1) Injection of adrenalin alone:

A first narrow peak in plasma adrenalin level occurred a few minutes following the injection and immediately decreased to basal level. A second much larger peak of similar height occurred 20 min later. The area under the curve (AUC) of this second peak was about 20 times higher than the first one indicating that the bulk of the injected dose reached the general circulation in a delayed manner, during this second period.

In a consistent manner, two hypertensive episodes occurred at the times of the plasma adrenalin peaks.
2) Injection of adrenalin combined with doxepin:

The AUC of plasma adrenalin, calculated on the first 10 min following the intramuscular injection, was increased by more than 500% whereas the total AUC remained unchanged when compared to AUCs obtained after the injection of adrenalin alone (see FIG. 1)

In other words, the association of doxepin to adrenalin strongly accelerated the bioavailability of the latter without modifying its total bioavailability.

In a consistent manner, the AUC of the hypertensive response during the first 10 min following the injection was enhanced by more than three folds. Plasma doxepin levels also peaked during these first 10 min and were maintained during the following two hours at concentrations several fold higher than required for continuous blockade of histamine H1 receptor, taking into account the below nanomolar affinity of the drug for this receptor.

Conclusion:

The synergy of adrenalin and doxepin resulted in almost immediate and enhanced hypertensive response as well as rapid and long lasting blockade of the H1 receptor, the stimulation of which is known to be at the origin of most of the deleterious effects of histamine released during an anaphylactic shock.

Example 2: Synergy of the Combination of Adrenalin with an Antidepressant in Guinea Pigs Protocol:

Groups of guinea pigs previously immunized against ovalbumine received the antigen and, at the beginning of the shock symptom appearance, received intramuscularly saline solution with adrenalin at 30 µg/kg alone, or in association with doxepin at 0.1 mg/kg.

Results:

An acceleration of the plasma bioavailability of adrenalin by doxepin was observed in this species as in rabbits.

In addition, whereas the mortality was of 90%, occurring after only 52±5 min, in adrenalin-treated animal mortality was of 81%, occurring after 57±7 min, two non significantly different values.

In contrast animals treated by adrenalin plus doxepin had significant decrease in mortality (to 62%) and significant increase in mortality delay (98±15 min).

Example 3: Synergy of the Combination of Adrenalin with an Antidepressant in Guinea Pigs Protocol:

Guinea pigs received intramuscularly saline solution with adrenalin at 30 µg/kg alone or in association with amitriptyline (1 mg/kg) or imipramine (1 mg/kg). Plasma levels of adrenalin were monitored.

Results:

An acceleration of the plasma bioavailability of adrenalin by amitriptyline and by imipramine was also observed in this species. Indeed, the AUC of plasma adrenalin, calculated on the first 15 min following the intramuscular injection of adrenalin with amitriptyline or imipramine, was increased by approximately 5 times compared to the corresponding AUC in animals receiving the injection of adrenalin alone.

What is claimed is:

1. A method for treating shocks comprising administering a single dosage immediately after shock to a subject in need thereof of an aqueous solution comprising adrenalin and an antidepressant, wherein the antidepressant is selected from the group consisting of amitriptyline, amoxapine, amitriptylinoxide, butriptyline, clomipramine, demexiptiline, dibenzepin, dimetacrine, dosulepin, doxepin, impiraminoxide, lofepramine, maprotiline, mianserin, melitracen, metapramine, nitroxazepine, nortriptyline, noxiptiline, pipofezine, propizepine, protriptyline, quinupramine, amineptine, trimipramine, and pharmaceutically acceptable salts thereof, wherein the adrenalin being administered comprises between 0.05 mg and 0.30 mg, wherein the antidepressant being administered comprises between 0.1 mg and 3 mg, and wherein the aqueous solution is administered by at least one intramuscular or subcutaneous injection.

2. The method according to claim 1, where the solution further comprises at least one or more agents selected from the group consisting of preservative agents, buffers and agents to make the solution isotonic with blood.

3. The method according to claim 1, wherein the antidepressant is doxepin or one of its pharmaceutically acceptable salts.

4. The method according to claim 1, wherein adrenalin is at a concentration comprising between 0.05 mg/ml and 1.0 mg/ml in said solution.

5. The method according to claim 1, wherein the antidepressant is at a concentration comprising between 0.1 mg/ml and 10 mg/ml in said solution.

6. The method according to claim 1, wherein said solution consists of adrenalin, an antidepressant, sodium chloride, a preservative agent and water.

7. The method according to claim 1 where said shock is selected from the group consisting of: anaphylactic shock, cardiac arrest, and cardiovascular distress associated with anaphylactic shock, hemorragic shock, traumatic shock, infectious shock and secondary shock due to cardiac surgery.

8. The method according claim 1 wherein the solution is administered by an auto-injector.

9. The method according to claim 1 wherein the adrenalin and antidepressant are administered in the same aqueous solution.

10. The method according to claim 1 wherein the adrenalin and antidepressant are administered in separate aqueous solutions.

* * * * *